US00PP18663P2

(12) United States Plant Patent
Bradford

(10) Patent No.: US PP18,663 P2
(45) Date of Patent: Mar. 25, 2008

(54) PLUM TREE NAMED 'REDYUMMY®'

(50) Latin Name: *Prunus salicina*
Varietal Denomination: REDYUMMY®

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/634,894

(22) Filed: Dec. 7, 2006

(51) Int. Cl.
*A01H 5/00* (2006.01)

(52) U.S. Cl. ..... Plt./184
(58) Field of Classification Search ..... Plt./184
See application file for complete search history.

(56) References Cited

U.S. PATENT DOCUMENTS

PP14,220 P2 10/2003 Bradford
PP14,247 P2 10/2003 Bradford

*Primary Examiner*—Kent Bell
*Assistant Examiner*—S. B. McCormick-Ewoldt

(57) ABSTRACT

The present invention relates to a plum tree and more particularly to a new and distinct variety broadly characterized by a large size, vigorous, hardy, and productive tree that is self-unfruitful and requires cross pollination. The fruit matures under the ecological conditions described during late August, with the first picking on Aug. 22, 2006, and will hang on the tree for about fifteen more days. The fruit is uniformly medium to large in size, full red in skin color, clingstone in type, globose to somewhat oblong in shape, mostly yellow in flesh color, very firm in texture, and very sweet in flavor.

1 Drawing Sheet

Botanical classification: *Prunus salicina.*
Varietal denomination: 'REDYUMMY®'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of plum tree, which has been denominated varietally as 'REDYUMMY®'. YUMMY® is a United States Trademark, Serial Number 75618722, owned by Johnny Appleseed Holdings Limited, Saint Georges Road South RD2, Hastings, New Zealand. Permission to use has been granted to the applicant by contract.

During a typical blooming season I isolate as seed parents both individual and groups of different plum trees by covering them with screen houses. A hive of bees is placed inside each such house, and bouquets to provide pollen from different plum trees are placed in buckets near the trees approximately every two days for the duration of the bloom. During 2001 one such house containing an unnamed red plum was crossed by me in this manner. To pollinate this red plum, I selected bouquets from several sources of plum trees without keeping specific written details. Upon reaching maturity the fruit from this red plum tree was harvested and the seeds were removed, cracked, stratified and germinated as a group with the label "H19P442". They were grown as seedlings on their own root in my greenhouse and upon reaching dormancy transplanted to a cultivated area of my experimental orchard located near Le Grand, Calif. in Merced County (San Joaquin Valley). During the summer of 2004 the claimed variety was selected by me as a single plant from the group of seedlings described above. Subsequent to origination of the present variety of plum tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to 'September YUMMY®' (U.S. Plant Pat. No. 14,220) plum by being self-unfruitful and by producing fruit that is full red in skin color, medium to large in size, and somewhat oblong in shape, but is distinguished therefrom by producing fruit that is purer yellow in flesh color, that is clingstone instead of semi-freestone, that is somewhat sweeter in flavor, and that matures about three weeks earlier.

SUMMARY OF VARIETY

The present plum variety is characterized by a large size, vigorous, hardy, and productive tree. Being self-unfruitful, the present variety requires cross pollination from a plum that blooms during the mid season, such as 'August YUMMY' (U.S. Plant Pat. No. 14,247). The present variety's abundance of blossoms and pollen entices strong bee activity to facilitate pollination. The fruit matures under the ecological conditions described during late August, with the first picking on Aug. 22, 2006, and will hang on the tree for about fifteen more days. The fruit is uniformly medium to large in size, full red in skin color, clingstone in type, globose to somewhat oblong in shape, purely yellow in flesh color, very firm in texture, and very sweet in flavor.

DRAWING

The accompanying photograph consists of four whole fruits positioned to display the characteristics of the skin color and form, one fruit divided transversely to the suture plane to reveal the flesh and stone, typical leaves, insets depicting the buds and blossoms as they appear on the tree, and a tip shoot.

DETAILED BOTANICAL DESCRIPTION

Referring now more specifically to the pomological characteristics of this new and distinct variety of plum tree, the following has been observed under the ecological conditions prevailing near Le Grand, Merced County (San Joaquin Valley), Calif. The fruit description was developed at the state of shipping ripe on Aug. 25, 2006, on the original tree during its fifth growing season. The flower and bud descriptions were developed during the previous blooming season. All major color code designations are by reference to the Inter-Society Color Council, National Bureau of Standards. Common color names are also used occasionally.

Parentage:

*Seed parent.*—Unnamed red plum.

*Pollen parent.*—Unknown.

Tree

Size: Large, reaching and maintaining a height of 12' [3.66 m.] and a spread of 9' [2.74 m.] after five growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to central leader form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually required.

Fertility: Self-unfruitful, requiring cross pollination by a suitable mid seasonal blooming plum, such as 'August YUMMY' (U.S. Plant Pat. No. 14,247).

Bearing: Reliable bearer, but dependent upon favorable weather during the blooming period.

Trunk:

*Size.*—Large, reaching a maximum diameter of 5" [127 mm.] after the fifth growing season.

*Texture.*—Shaggy.

*Bark color.*—A Dark grayish brown [62. d.gy.Br] and Olive gray [113. OlGy] variegation with Strong yellowish brown [74. s.yBr] crevices present.

*Lenticels.*—Approximate Number Per Square Inch: 12. Color: Strong yellowish brown [74. s.yBr]. Typical Size: 3/16" [4.8 mm.] to 9/16" [14.3 mm.]. Shape: Eye-shaped to elongated.

Branches:

*Size.*—Diameter of first lateral is 1" [25 mm.] measured 12" from the central leader.

*Texture.*—Smooth on first and second year wood, increasing roughness with age.

*Color.*—1st Year Wood Topside: Deep yellowish brown [75. deep yBr]. 1st Year Wood Underside: Brilliant yellow green [116. brill.YG]. Older Wood: Deep yellowish brown [75. deep yBr].

*Lenticels.*—Number Per Square Inch: More than 60 on second year wood. Color: Light yellowish brown [76. l.yBr]. Typical size: 1/32" [0.8 mm.] to 3/32" [2.4 mm.]. Shape: Elongated.

Leaves:

*Size.*—Large. Average Length: 4 3/8" [111 mm.]. Average width: 1 7/8" [48 mm.].

*Arrangement.*—Alternate.

*Thickness.*—Medium.

*Form.*—Elliptical.

*Apex.*—Acuminate.

*Base.*—Acute with an average angle base angle of 80 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: 11/16" [17.5 mm.]. Average Thickness: 1/16" [1.6 mm.]. Color: Light yellow green [119. l.YG].

*Stipules.*—Number: 2 per leaf, up to 6 per growing tip. Average Length: 7/16" [11.1 mm.]. Color: Light yellow green [119. l.YG] becoming Light reddish brown [42. l.rBr] with age.

*Glands.*—Number: Usually 2 to 4 per leaf. Position: Both opposite and alternate, the first pair located at the intersection of the petiole and leaf with the rest positioned on the leaf blade. Size: Small. Form: Globose. Color: Light yellow green [119. l.YG] acquiring Moderate brown [58. m.Br] centers with age.

*Leaf buds.*—Pointed, medium.

Flower buds:

*Hardiness.*—Hardy, with respect to central California winters.

*Diameter.*—Typically 3/16" [4.8 mm.] 1 week before bloom.

*Length.*—Typically 3/8" [9.5 mm.] 1 week before bloom.

*Form.*—Not appressed.

*Surface.*—Pubescent.

*Color.*—White [263. White].

Flowers: Perfect, complete, perigynous, usually a single pistil, typically twenty-four or more stamens, five sepals and petal locations alternately positioned.

*Average flower diameter.*—1" [25.4 mm.].

*Number of petals.*—Five, no double blossoms observed.

*Petal shape.*—Circular to oval.

*Petal margin.*—Smooth.

*Average petal diameter.*—7/16" [11.1 mm.].

*Average petal length.*—1/2" [12.7 mm.].

*Petal apex.*—Rounded.

*Petal base.*—Rounded to somewhat obtuse.

*Petal color.*—White [263. White].

*Anther color.*—Brilliant yellow [83. brill.Y].

*Stigma color.*—Pale greenish yellow [104. p.gY].

*Sepal color.*—Light yellow green [119. l.YG] with Grayish pink [8. gy.Pk] toward the margins.

*Sepal length.*—5/32" [4.0 mm.].

*Sepal width.*—1/8" [3.2 mm.].

*Average pistil length.*—5/8" [15.9 mm.].

*Average stamen length.*—1/2" [12.7 mm.].

*Fragrance.*—Moderate.

*Pollen production.*—Moderate.

*Blooming period.*—Medium, two days before 'September YUMMY' (U.S. Plant Pat. No. 14,220).

*Onset of bloom.*—One percent on Feb. 20, 2006.

*Date of full bloom.*—Mar. 4, 2006.
*Duration of bloom.*—One to two weeks, dependent on ambient temperature.
*Bloom density.*—Heavy.
*Number per cluster.*—2 to 8, 3 most often.

FRUIT

Maturity when described: Shipping ripe, Aug. 25, 2006.
Date of first picking: Aug. 22, 2006.
Date of last picking: Sep. 7, 2006.
Size: Uniform, medium to large.
*Average diameter axially.*—2 13/16" [71 mm.].
*Average diameter across cheek plane.*—2¾" [70 mm.].
*Average diameter across suture plane.*—2 13/16" [71 mm.].
*Typical weight.*—6.8 ounces [193 grams].
Form: Uniform, symmetrical, globose to slightly oblong on some.
*Longitudinal section form.*—Oval.
*Axial view.*—Round.
Suture: An inconspicuous line located in shallow groove extending from the base to apex.
Ventral surface: Rounded, no lips.
Cavity: Flaring, somewhat elongated in the suture plane, suture showing on one side, Pale yellow [89. p.Y] stem markings on some.
*Depth.*—⅜" [9.5 mm.].
*Breadth.*—⅞" [22.2 mm.].
Base: Truncate.
Apex: Rounded with a slight hump at the pistil point on about half.
Pistil point: An inconspicuous dot.
Stem: Medium.
*Average length.*—⅜" [9.5 mm.].
*Average width.*—⅛" [3.2 mm.].
Skin:
*Thickness.*—Medium.
*Surface.*—Smooth.
*Tenacity.*—Tenacious to flesh.
*Taste.*—Slightly astringent.
*Tendency to crack.*—Slight.
*Color.*—Moderate red [15. m.R] to Dark red [16. d.R] with moderate Light orange yellow [70. l.OY] freckling throughout.
*Bloom.*—Abundant.
Flesh:
*Color.*—Pale yellow [89. p.Y] with a very slight amount of Deep pink [3. deep Pk] bleeding very near the skin.
*Surface of pit cavity.*—Light yellow [86. l.Y] broken fibers when twisted away from stone.
*Amygdalin.*—Moderate.
*Juice.*—Abundant, rich.
*Texture.*—Firm, crisp.
*Fibers.*—Abundant, fine.
*Ripens.*—Fairly even.
*Flavor.*—Acidic and very sweet, typically 21 brix.
*Aroma.*—Very slight.
*Eating quality.*—Very good.

STONE

Type: Clingstone.
Form: Oval.
Hilum: Narrow.
Base: Oblique.
Apex: Obtuse with an average angle of 110 degrees.
Sides: Equal.
Surface: Rough throughout, with characteristic grooves on each side of the dorsal fin.
External color of stone: Light brown [57. l.Br].
Pit wall color when cracked: Light yellowish brown [7.6. l.yBr].
Cavity surface color: Deep brown [56. deep Br].
Average pit wall thickness. 1/16" [1.6 mm.].
Average width: ¾" [19.1 mm.].
Average length: —1" [25.4 mm.].
Average breadth: ⅜" [9.5 mm.].
Tendency to split: Slight.
Kernel:
*Form.*—Oval.
*Skin color.*—Strong yellowish brown [74. s.yBr].
*Pellicle color.*—Grayish brown [61. gy.Br].
*Vein color.*—Deep brown [56. deep Br].
*Taste.*—Bitter.
*Viable.*—Yes.
*Average width.*—7/16" [11.1 mm.].
*Average length.*—⅝" [15.9 mm.].
*Amygdalin.*—Abundant.

USE

Market: Fresh market and long distance shipping.
Keeping quality: Excellent, fruit quality observed to remain in good condition after 35 days in standard cold room at 36° Fahrenheit [2° Celsius].
Shipping quality: Excellent.
Resistance to insects: No unusual susceptibilities noted.
Resistance to diseases: No unusual susceptibilities noted.
Resistance to heat: No damage observed following extended period of temperatures in excess of 110 degrees Fahrenheit during July of 2006.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is most similar to 'September YUMMY®' (U.S. Plant Pat. No. 14,220) plum by being self-unfruitful and by producing fruit that is full red in skin color, medium to large in size, and somewhat oblong in shape, but is distinguished therefrom by producing fruit that is purer yellow in flesh color, that is clingstone instead of semi-freestone, that is somewhat sweeter in flavor, and that matures about three weeks earlier.

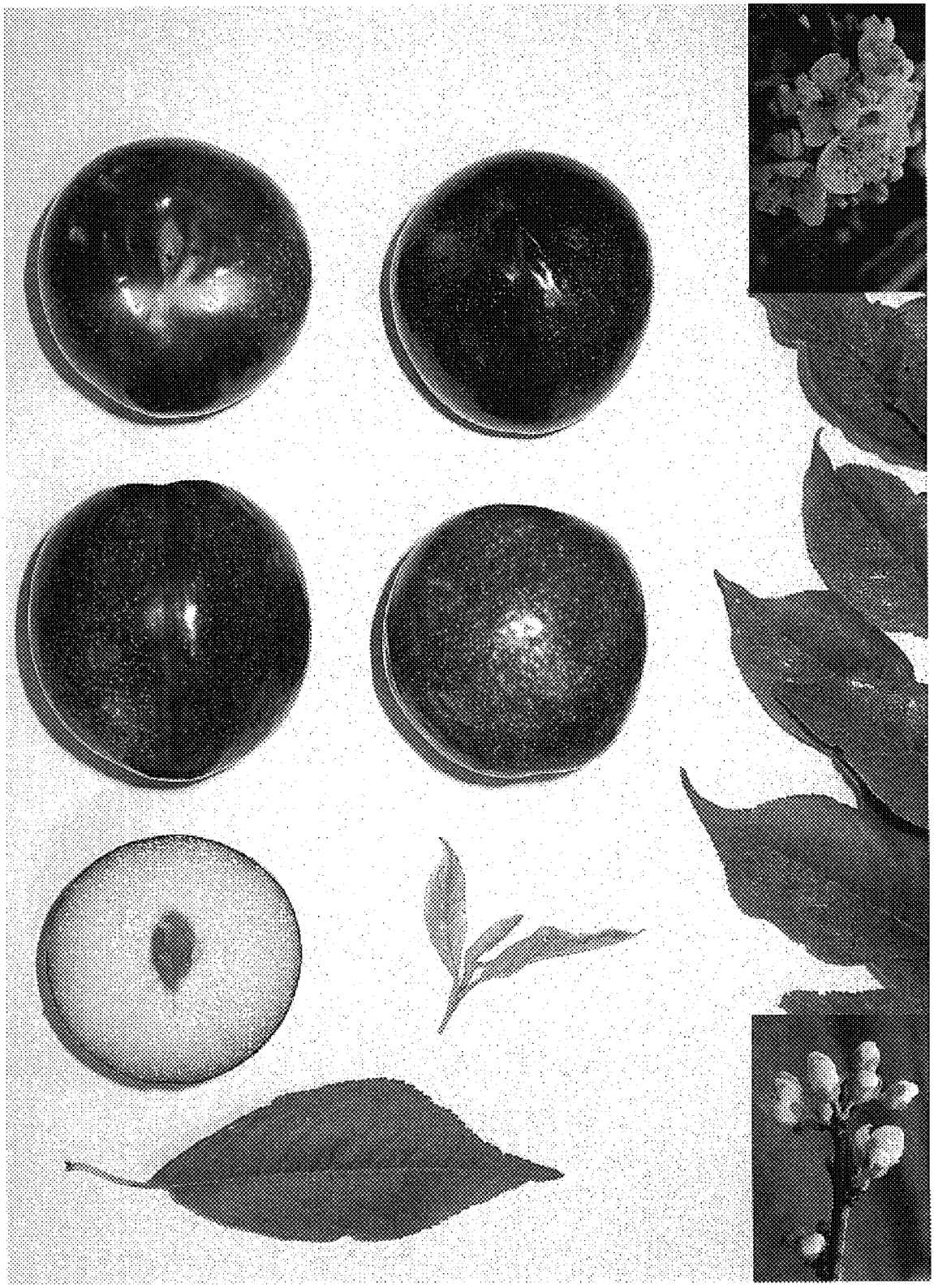

* * * * *